(12) United States Patent
Harris

(10) Patent No.: US 6,573,073 B2
(45) Date of Patent: Jun. 3, 2003

(54) CFTR GENE REGULATOR

(75) Inventor: Ann Harris, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 09/142,913

(22) PCT Filed: Mar. 20, 1997

(86) PCT No.: PCT/GB97/00787

§ 371 (c)(1),
(2), (4) Date: Sep. 18, 1998

(87) PCT Pub. No.: WO97/35005

PCT Pub. Date: Sep. 25, 1997

(65) Prior Publication Data

US 2002/0086836 A1 Jul. 4, 2002

(30) Foreign Application Priority Data

Mar. 20, 1996 (GB) .............................. 9605808

(51) Int. Cl.⁷ ............................... C12N 15/64
(52) U.S. Cl. .................. 435/91.4; 435/69.1; 435/320.1; 435/325; 435/455; 536/23.1; 536/24.1; 536/24.3; 536/25.3; 536/24.33
(58) Field of Search ......................... 514/44; 424/93.2; 435/320.1, 91.4, 455, 458; 536/23.1, 24.5, 24.1, 24.3, 24.33, 25.3

(56) References Cited

FOREIGN PATENT DOCUMENTS

| EP | 0 181 634 A | 5/1986 |
|---|---|---|
| WO | WO 91 10734 A | 7/1991 |
| WO | WO 95 16028 A | 6/1995 |

OTHER PUBLICATIONS

Verma et al., Nature, vol. 389, pp. 239–242, 1997.*
Anderson, Nature, vol. 392, pp. 25–30, 1998.*
Gunzburg et al., Molecular Medicine Today, 1, 9, pp. 410–417, 1995.*
Boucher (TIG vol. 12, 3, pp. 81–84), 1996.*
Gene Bank Database, AN: D2085, 1992.*
J Biol Chem, Apr. 26, 1996, 271 (17) P9947–54, United States, XP002037939 Smith an et al: "A regulatory element in intron 1 of the cystic fibrosis transmembrane conductance regulator gene." See the whole document.
J. Med. Virol., vol. 47, 1995, pp. 145–152, XP002037940 Ando T et al? "Epidemiologic applications of novel molecular methods to detect and differentiate small round structured viruses (Norwalk–like viruses)" see figure 2.
J Biol Chem, May 15, 1991, 266 (14) P9140–4, United Stattes, XP002037941 Yoshimura K et al? "The cystic fibrosis gene has a "housekeeping"–type promoter and is expressed at low levels in cells of epithelial origin." Cited in the application.
Journal of Biological Chemistry, vol. 268, No. 21, 1993, MD US, pp. 15912–15921, XP002037942 Koh J et al: "Characterization of the cystic fibrosis transmembrane conductance regulator promoter region" cited in the application.
Biochem Biophys Res Commun, Jun. 6, 1995, 211 (1) P274–81, United States, XP000677841 Smith An et al: "Characterization of DNASE I hypersensitive sites in the 120kb 5' to the CFTR gene".

* cited by examiner

*Primary Examiner*—Dave Trong Nguyen
(74) *Attorney, Agent, or Firm*—Nixon & Vanderhye P.C.

(57) ABSTRACT

The invention relates to a novel CFTR gene regulatory element capable of increasing the activity of the CFTR gene promoter, and to nucleic acid constructs comprising the element together with the CFTR gene coding region. The element and constructs containing it are useful in gene therapy for treating cystic fibrosis.

9 Claims, 1 Drawing Sheet

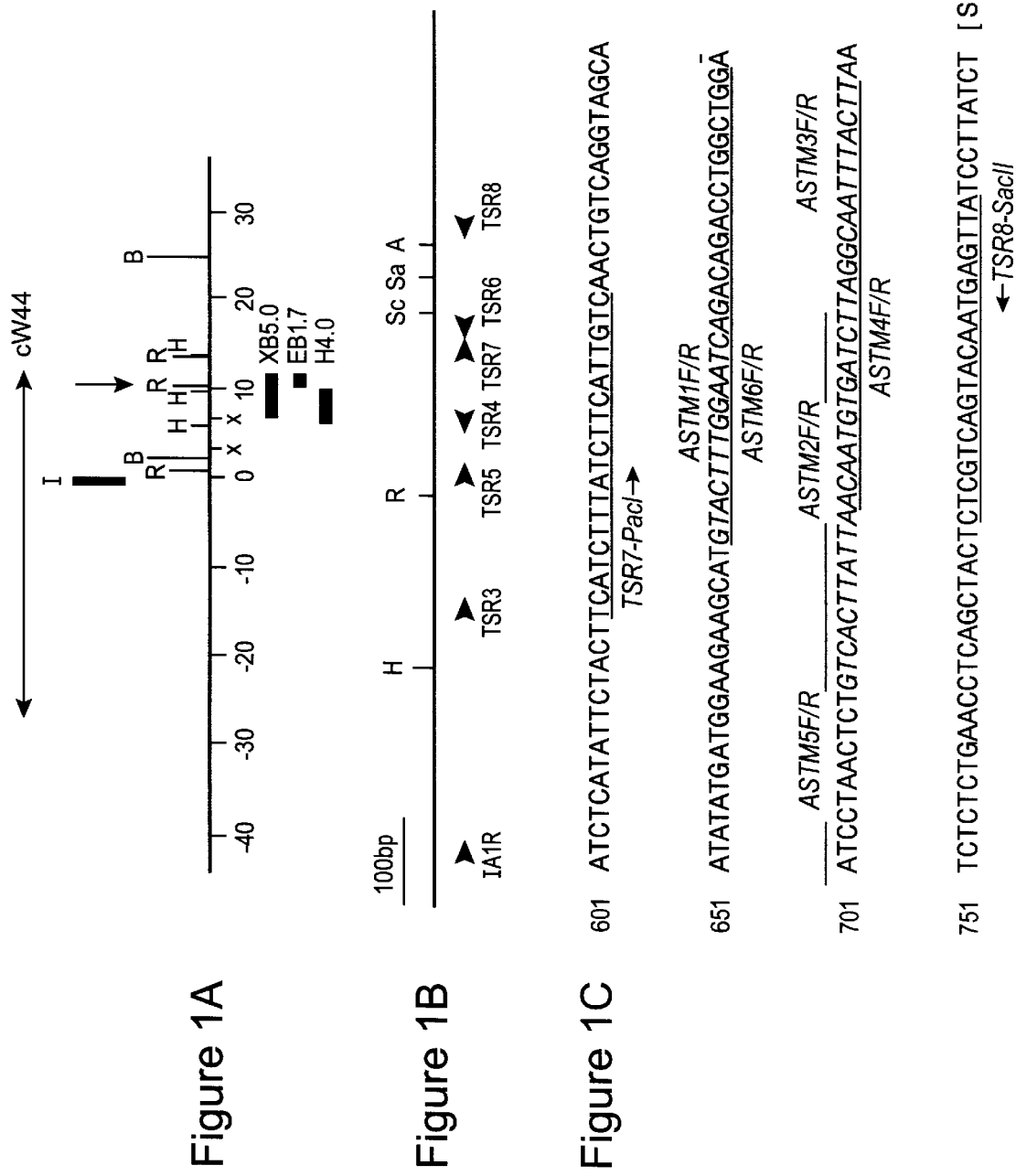

CFTR GENE REGULATOR

This is a 371 of PCT/G597/00787, filed Mar. 20, 1997.

Cystic fibrosis (CF) is one of the most common serious inherited diseases amongst Caucasians. One in 20–25 people harbour a mutation in the CF gene. As CF is an autosomal recessive syndrome this means that around 1 in 2,000 live births are affected. CF affects many organs including sweat glands (cystic fibrosis sufferers have salty sweat), the gut and the pancreas (85% of CF patients are pancreatic insufficient and require enzyme supplements in the diet). However, it is the effects on the lung which are most commonly life-threatening and lead to premature death. Specifically, cystic fibrosis patients accumulate mucus in the airways which is only relieved by regular physiotherapy. This mucus serves as a substrate for bacterial infection resulting in lung damage. More recently it has been shown that the cystic fibrosis lung milieu inactivates naturally occurring anti-microbial defences. The gene for cystic fibrosis was identified and sequenced in 1989 and subsequent studies showed that the gene product is a cAMP-activated chloride channel in the membrane of specialised epithelial cells.

Cystic fibrosis is an ideal model disease for gene therapy. First, it is a single gene disorder. Second, the most important target cells, within the airway epithelium, are accessible by non-invasive techniques. Third, at least one function of the CF gene product is known, allowing ready determination of whether the gene has been delivered and expressed in a functional form.

The cystic fibrosis transmembrane conductance regulator (CFTR) gene shows a tightly regulated pattern of temporal and spatial expression. Very little is known about the genetic elements and transcription factors that regulate CFTR expression. The basal promoter of the CFTR gene has been analysed in some detail though the data are somewhat inconsistent (Chou, J.-L. et al (1991) J. Biol. Chem. 266: 24471–24476; Yoshimura, K. et al (1991) Nucleic Acids Res. 19: 5417–5423; Yoshimura, K. et al (1991) J. Biol. Chem. 266: 9140–9144; Koh, J. et al (1993) J. Biol. Chem, 268: 15912–15921). The minimal promoter sequence found between −226 and +98 bp with respect to the major transcription site is sufficient to drive low levels of expression of a reporter gene There is little data on the control of cell specificity of CFTR expression though there is ample evidence for such regulation. The human CFTR gene is expressed at significant levels mainly in the epithelia lining the pancreas, intestine, bile ducts, mate genital ducts and in certain regions of the airway epithelium including the inferior turbinate of the nose, the trachea and the serous portion of submucosal glands. There is IS evidence that expression of the CFTR gene may be hormonally regulated in epithelia within the reproductive system. Some degree of cell type specific control has been inferred for uncharacterised elements within the immediate 5' untranslated region. DNAse I hypersensitive sites (DHS) are often associated with regulatory elements. A number of these sites that show some degree of correlation with CFTR expression have been observed between −3,000 bp relative to the transcription start site and +100 bp into intron 1. However these sites have only been examined in a few long-term cell lines that either do or do not express CFTR mRNA and protein and hence may not adequately reflect cell specific regulation of expression of the CFTR gene in vivo.

Since the expression control elements of the CFTR gene had not been well defined the inventor screened a larger region of genomic DNA than had been analysed previously in an attempt to identify these elements. The chromatin structure of 120 kb of genomic DNA 5' to the CFTR gene was analysed in a number of CFTR expressing and non-expressing cell types, including primary genital duct epithelial cells in addition to long term cell lines. The inventor identified DNAse I hypersensitive sites within this region by screening with probes isolated from cosmid and phage clones. Novel DNAse I hypersensitive sites were observed at −79.5 kb and −20.5 kb 5' to the ATG translation start codon of the CFTR coding sequence. Neither of these sites showed strong correlation with CFTR expression in the cell types investigated. Although they may play an important role in the complex series of events involved in the regulation of CFTR transcription, these data do not support the existence of cell specific control elements at these sites.

A Novel DNAse I Hypersensitive Site in Intron 1

More recently, the inventor identified a DNAse I hypersensitive site 10 kb downstream of the 3' end of exon 1 of the CFTR gene. The presence of this site correlated well, quantitatively and qualitatively, with the levels of expression of the CFTR gene in both long term cell lines and primary genital duct epithelial cells. This is the first intronic regulatory element to be reported for the CFTR gene. Its location may, in part, explain the failure of several groups to elucidate the elements involved in regulating control of expression of CFTR, since previous analyses of the CFTR promoter region have been restricted to sequences 5' to and including the first exon. These findings are described in Smith, A. N. et al (1996) J. Biol. Chem. 271: 9947–9954.

FIG. 1A shows the location of the intron 1 DNAse I hypersensitive site and the relative positions of the XB5.0, H4.0 and EB1.7 subfragments of the cW44 cosmid that were used as probes to detect this site. Increasing amounts of DNAse I revealed a hypersensitive site within this 22 kb fragment yielding a major product of 8 kb. The hypersensitive site was located approximately 10 kb 3' to the end of exon 1 of the CFTR gene. Based on CF Genetic Analysis Consortium nomenclature this site has been called 181+10 kb, where 181 refers to the last base in exon 1. This hypersensitive site has the potential to contain cell type expression control elements as it is seen only in cell lines that transcribe CFTR mRNA. As shown in Table 1 below, the relative degree of hypersensitivity of the site correlated with the relative levels of endogenous expression of CFTR. The high expressing colon carcinoma cell lines Caco2 and HT29 show the site most strongly; the pancreatic adenocarcinoma cell line Capan that expresses low levels of CFTR mRNA shows the hypersensitive site weakly and the breast carcinoma epithelial cell line MCF7 and the lymphoblastoid cell line 37566 do not show this site. Most importantly, cultured human fetal epididymis and vas deferens epithelial cells that express CFTR in vitro show the hypersensitive site.

The 1 kb of DNA that spans the hypersensitive site has been cloned and sequenced and a partial restriction map of 850 bp flanking this region is shown in FIG. 1B. The nucleotide sequence has been submitted to the GenBank/EMBL Data Bank with accession number U47863.

Electrophoretic Mobility Shift Assays (EMSA) AND DNAse I Footprinting

Overlapping fragments of approximately 200 bp, 3/4 (TSR3-TSR4), 5/6 (TSR5-TSR6), and 7/8 (TSR7-TSR8) from within the 850 bp fragment of intron 1 were generated by PCR (see FIG. 1B and Table 2). No specific gel mobility shifts were observed with fragments 3/4 or 5/6. However several proteins bound to fragment 7/8. Two gel mobility shift bands were generated by nuclear extracts from all cell lines tested, irrespective of whether they transcribe CFTR. At least one other protein complex was seen in longterm cell lines transcribing CFTR, Caco2 and HT29. Primary epididymis and primary vas deferens nuclear extracts also caused gel mobility shifts of fragment 7/8 and the formation of a complex of at least 3 components. These protein DNA complexes were specifically competed by excess cold fragment 7/8 but not by the 5/6 fragment.

Further mapping of the location of the DNA protein complexes detected by EMSA was achieved by competition with subfragments of the 7/8 element. Subsequent DNAse I footprinting of the 7/8 fragment following binding of nuclear extracts from the MCF7 and HPAF cells lines that do not transcribe CFTR, the Caco2 carcinoma cell line and two independent primary epididymis cell cultures that transcribe the CFTR gene revealed several regions of protection in the CFTR expressing cell lines and one region that was common to all cell types. It is probable, given the complexity of the DNAse I footprint and EMSA data, that a number of proteins are interacting with this region of genomic DNA. Further EMSA with oligonucleotides chosen on the basis of the DNAse I footprints has narrowed the DNA protein interactions that generate the gel mobility shifts seen with all nuclear extracts to a minimum of 13 bp. The DNA protein interactions that generate the gel mobility shifts, seen in Caco2 and HT29 and those seen in primary epididymis nuclear extracts involve a minimum of 9 bp lying 5' to the region involved in the above complex.

Transient Transfection Reporter Gene Assays

In vitro transient assays of the activity of the regulatory element (the BSO.7 fragment [IA1R-TSR8] spanning the 181+10 kb site, see FIG. 1B,) have shown that it augments the level of the CFTR promoter mediated expression of the luciferase reporter gene in the Caco2 cell line by a mean of 3.4 fold in 30 independent transfections. Though this enhancement of expression might seem relatively modest this is not unexpected given the weak activity of the CFTR promoter in driving reporter gene expression in transient assays. Moreover, the observed enhancement of expression is of the same order of magnitude as has been observed for other regulatory elements in the CFTR gene promoter.

The constructs used in the transient transfections contained the 787 bp CTFR basal promoter fragment (designated 245) driving luciferase expression with the 5/6, 7/8 or BSO.7 (IA1R-TSR8) fragments cloned into the enhancer site of the PGL2B vector (3' to the CFTR promoter). These were co-transfected with pdolCMVcat (Ma, Y.-G. et al (1992) Dev. Biol. 154: 45–54) into the Caco2 cell line and both CAT and luciferase activities were assayed.

The 181+10 kb Regulatory Element in Airway Epithelial Cells

One of the important questions relating to the intron 1 regulatory element was whether it is significant in airway epithelium. The bronchial carsinoma cell line Calu 3 (Haws, C., et al (1994) Am. J. Physiol. 266:; L502–L512), which expresses CFTR endogenously, has now been analysed and the 181+10 kb DHS is evident in confluent cultures of Calu 3 cells. Further, Nuclear extracts from Calu 3 cells contain proteins that bind specifically to the regulatory element DNA, and give an EMSA profile that is very similar to that seen with nuclear extracts of primary epididymal cells. These results will be confirmed with other airway epithelial cells with a less plastic phenotype than Calu 3.

Analysis of the 181+10 kb Regulatory Element in Mice Transgenic for a Human CFTR YAC A transgenic mouse has now been generated in which a human CFTR YAC (37AB12) has been used to correct the CF phenotype of the Cambridge CF null mice. The chromatin structure of the human CFTR transgene in this mouse has been analysed. Nuclei were extracted from mouse tissues that do or do not express the human CFTR transgene and the presence or absence of the 181+10 kb DHS was examined. Data show the appearance of the DNAse hypersensitive site in small intestine and kidney, which both express the human transgene, but the DHS is absent from liver and testis, which do not express the human CFTR gene. These data suggest that the regulatory element in intron 1 is of functional importance in mice in vivo (Manson et al (1997) Complementation of Null CF mice with a human CFTR transgene, submitted).

BRIEF DESCRIPTION OF THE DRAWINGS

In the accompanying drawings, FIG. 1 is in three parts A, B and C as follows:—

A. Long Range Map of 70 kb of Genomic DNA Flanking Exon I of the CFTR Gene

The restriction map for relevant sites for the enzymes BamHI(B), EcoRI(R), HindIII(H) and Xho1(X) is shown above the solid line. The scale is in kilobases, where zero denotes the position of the ATG start codon of the CFTR coding sequence. I denotes the location of exon 1. The cosmid cW44 used as a source of probes is indicated by the horizontal arrow. The solid boxes represent the cW44 XB5.0, H4.0 and EB1.7, probes used to detect the novel DNAse 1 hypersensitive site at 181+10 kb. The vertical arrow marks the location of this site.

B. The Restriction Map of 800 bp Flanking the 181+10 kb DNAse I Hypersensitive Site.

The sites of the primers used to amplify segments 3/4, 5/6, 7/8 and the BSO.7 (IA1R-TSR8) fragment are shown by arrows. The HindIII (H) and EcoRI (R) restriction sites shown close to the hypersensitive site in FIG. 1A are shown, also Scrf1 (Sc), Sau3a (Sa) and Alu (A) restriction sites in the 7/8 fragment.

C. The CFTR Gene Regulatory Element Sequence.

The numbers 601, 651, 701, 751 are arbitrary; on that scale, the 5' end of IA1R is 37 and the 3' end of TSR8 is 792. Oligonucleotides used in competition experiments are shown as follows: in italics ASTM1F/R, ASTM2F/R, ASTM3F/R (in bold); ASTM4F/R and ASTM6F/R underlined; ASTM5F/R overlined. There is a Mse1 restriction site at 720.

Through a combination of the above DNAse I footprint analysis and gel mobility shift assays using sub-fragments of the region (7/8) containing this element and the above ASTM1-6FIR oligonucleotides, the inventor has determined that the regulatory element is located within a sequence of about 40 bp. The 40 bp sequence contains two distinct sites of DNA-protein interactions (FIG. 1C). The 5' side of the Mse I site at 720 bp contains the sequence AATC-CTAACTCT<u>GTCACTTAT</u> [SEQ ID NO:1]. A minimum of 9 bases (underlined) at the end of this sequence is crucial for the binding of the proteins found specifically in the nuclear extracts of the CFTR-expressing Caco2 and primary epidymal cells. It is probable that additional base pairs may be involved in the interaction. On the 3' side of the same Mse I site is the sequence TA<u>ACAATGTGATCTTAGGCAATTTACTT</u> [SEQ ID NO:2]. A minimum of 13 base pairs (underlined) are likely to be involved in DNA binding of the proteins that generate the c1 and c2 complexes detected in CFTR expressing and non-expressing cells.

The invention provides as new compounds these two motifs ([SEQ ID NO:1 and SEQ ID NO:2]) both separately and together contiguously or otherwise, (since they may well interact in vivo) and fragments thereof including one or both of the underlined sequences. Since it is likely that the flanking sequences may also exert a subsidiary regulating function, the invention also includes:

Nucleic acid elements containing up to 200 nucleotide residues including at least one defined oligonucleotide and having at least 70% homology with part or all of the sequence shown in FIG. 1C;

Nucleic acid elements that are capable of controlling expression of the human CFTR gene and which have at least 70% homology with part or all of the sequence shown in FIG. 1C.

Nucleic acid elements that are capable of controlling expression of the CFTR gene and which include a functional sequence at least 4 or 5 nucleotides in length and contained within one of the sequences set out above.

Nucleic acid elements that are capable of controlling expression of the CFTR gene and which are derived from intron 1 of the CFTR gene, in particular from the 850 bp intron 1 sequence in GenBank/EMBL Data-Bank under accession number U47863.

Elements "derived from intron 1" include elements obtained from intron 1 using molecular biology techniques, and synthetic elements corresponding to identified elements in intron 1. The elements are not necessarily identical to the native elements; they may be altered in a variety of ways using well-known techniques, for example to enhance their regulatory function.

The sequence TTAACAATGTGATCT [SEQ ID NO:3] at 720–734 shows homology to a consensus negative glucocorticoid response element that is widely distributed in the genome.

Gene Therapy

The CFTR gene is about 250 kb in length. The coding sequence comprises 18 exons and is in total about 6.5 kb in length. The DNA hitherto used for CF gene therapy has always been simple CFTR cDNA, i.e not containing any intronic material.

Two gene delivery systems are currently being tested for cystic fibrosis gene therapy, adenoviruses and liposomes. In the United States several research groups have conducted clinical trials using adenoviral vectors. These contain CFTR cDNA with a viral promoter to drive transcription; the 6.5 kb length of the cDNA is convenient for insertion in a vector. Results have been mixed. Trials on individual patients using adenoviral vectors to deliver the cDNA to the nasal epithelium, have reported some success. However the most complete double blinded trial recently published reported a failure to deliver a functional CF gene. Importantly, the dose of adenoviruses which could be used was limited because of the inflammatory responses generated.

In Britain, liposomes have been the delivery system of choice, and several research teams are co-operating in the development of liposome delivery systems for cystic fibrosis. In these systems also, the DNA used has been CFTR cDNA. Although liposomes are less efficient than adenoviral vectors at delivering DNA, they have the advantage of not being inflammatory or immunogenic.

Whatever the delivery system used, the idea of gene therapy is that the DNA in question will be introduced into human cells, in an episomal (non-integrated) or integrated form, and will there express the CFTR protein which acts as a chloride ion channel. Of the many potential problems, one is relevant here. The CFTR gene promoter is by itself not very active. By contrast, the CFTR gene is expressed at a high level in vivo in the serous portion of sub-mucosal glands in the lungs. The DNA administered in the course of gene therapy will in principle be expressed in all human cells in which it becomes incorporated. This is because the viral and other promoters hitherto used do not have any cell specificity. But the desired effect of gene therapy is that the CFTR gene should be expressed in, and only in, those cells where it would be expressed in a normal healthy individual. There is a need for a promoter system that regulates spatial expression of the CFTR gene.

The present invention addresses this need.

In another aspect, the invention provides a nucleic acid construct up to 50 kbp in length comprising the coding sequence of the CFTR gene together with a nucleic acid element as described above. The specified maximum length of 50 kbp is not critical, and longer constructs are envisaged which are, however, much shorter than the complete CFTR gene. Preferably the length of the construct is such that the construct can conveniently be incorporated in a viral or other vector for administration.

The nucleic acid regulator that is provided in this construct is preferably present between exon 1 and exon 2 of the coding sequence of the CFTR gene. However, elements of this kind sometimes have powerful long-distance effects that are independent of their position or orientation in the gene. So it is envisaged that this element may alternatively be present, together with the promoter upstream of exon 1, or intermediate some other pair of exons comprising the gene, or even at the downstream end of the coding sequence of the gene, provided that the regulator is positioned so as to be capable of modulating expression of the CFTR gene.

Preferably a CFTR gene promoter sequence is also present, operably linked to the CFTR gene and generally in a functional position at the upstream end of the coding sequence of the gene.

In other aspects, the invention further provides:

A vector containing a nucleic acid construct as defined; and a method of treating by gene therapy a patient suffering from cystic fibrosis which method comprises administering to the patient this vector.

A method of preparing an agent for treating cystic fibrosis by gene therapy, which method comprises bringing a nucleic acid construct as defined into a form suitable for administration. For this purpose, the following steps are envisaged:— i) Place the CFTR cDNA in a vector where it is driven by its own promoter rather than by a viral one, despite the relative weakness of the CFTR promoter.

ii) Modify the CFTR cDNA by PCR-mutagenesis to insert the splice donor site at the end of exon 1 (within intron 1) and the splice acceptor site of exon 2 (also within intron 1). At the same time also insert about 600 bp of known intron 1 sequence, about 250 bp adjacent to exon 1 and 250 bp adjacent to exon 2 and in the centre the regulatory element. This construct would then, due to the presence of the relevant splice sites, be capable of splicing out the inserted mini-intron 1 and generate a normal full length CFTR cDNA in human cells. The construct would be tested for this ability.

iii) An alternative stratagem would be to insert the regulatory element directly into the vector backbone either upstream of the CFTR promoter or downstream of the CFTR cDNA.

The invention is not limited with regard to the vector system, although adenovirus and liposome delivery systems may be preferred. Alternative vectors which may be employed include for example retroviral vectors.

Details of vectors which may be useful for gene therapy for CFTR, and of their construction, can be found in the published literature for example Boucher, R. C. et al (1994) Human Gene Therapy 5: 615–639 (adenovirus vectors); Zabner, J. et al (1993) Cell 75: 205–216 (adenovirus vectors); Caplen, N. J. et al (1994) Gene Therapy 1: 139–147 (liposome-mediated DNA transfer); Caplen, N. J. et at (1995) Nature Med. 1: 39–46 (liposome-mediated DNA transfer). In accordance with the present invention, similar strategies may be used, but employing the regulatory element described herein and the CFTR promoter. The literature also describes transfer of the CFTR gene to target cells, both in vitro and in vivo, including suitable pharmaceutically acceptable formulations and protocols for administration.

Although the invention is described herein in relation to the human CFTR gene and its regulators, animal models are not excluded. The regulatory elements, nucleic acid constructs, vectors and uses of all of these may therefore be from and/or for use in non-human mammals.

TABLE 1

EXPRESSION OF CFTR AND PRESENCE OF DNASE 1
HYPERSENSITIVE SITE AT 181 + 10 kb

The relative level of CFTR expression in the cell types used, based on the RT-PCR results and the prominence of the DNAse I hypersensitive site

| Cell Type | Presence of 181 + 10 kb site | Level of CFTR Expression |
| --- | --- | --- |
| HT-29 | + + | + + + |
| Caco-2 | + + | + + + |
| Capan-1 | + | + |
| primary vas deferens epithelial cells (vas) | + | + |
| primary epididymis epithelial cells (epid) | + + | + + |
| immortalized vas deferens epithelial cells (RVP) | +/− | +/− |
| immortalized epididymis epithelial cells (REP) | +/− | +/− |
| MCF7 | − | − |
| lymphoblastoid line (37566) | − | − |

Key: For the presence of the DNAse I hypersensitive site: + + most prominent; + clearly visible; +/− just visible; − absent.
For the level of CFTR expression: + + + maximum, + + moderate; + low level; +/− just detectable by RT-PCR; − undetectable.

What is claimed is:

1. The isolated oligonucleotide GTCACTTAT or oligonucleotide complementary thereto.

2. The isolated oligonucleotide ACAATTGATCTT (SEQ ID NO:25) or oligonucleotide complementary thereto.

3. An isolated oligonucleotide which is one of the following sequences; a fragment of one of the following sequences, which fragment includes one or both of the underlined sequences; or an oligonucleotide fully complementary to one of the following sequences or to said fragment:

AATCCTAACTCT<u>GTCACTTAT</u> (SEQ ID NO: 1),

TA<u>ACAATGTGATCTT</u>AGGCAATTTACTT (SEQ ID NO: 2),

AATCCTAACTCT<u>GTCACTTAT</u>TA<u>ACAATGTGATCTT</u>AGGCAATTTACTT
(SEQ ID NO: 23).

4. An isolated nucleic acid element containing up to 200 nucleotide residues which includes the oligonucleotide of any one of claims to 1 and 3 which has at least 70% homology with the sequence of SEQ ID NO:24 or a fragment thereof.

5. An isolated nucleic acid element including a functional sequence, which functional sequence is contained within the sequence of SEQ ID NO:1, SEQ ID NO:2 or SEQ ID NO:23, and which nucleic acid element controls expression of the CFTR gene and which nucleic acid element is not TGTCACTTATCTTGC (SEQ ID NO:26).

6. An isolated nucleic acid construct up to 50 k bp in length comprising the coding sequence of the CFTR gene together with the nucleic acid element according to claim 4.

7. The isolated nucleic acid construct as claimed in claim 6, wherein the nucleic acid element is present between axon 1 and axon 2 of the coding sequence of the CFTR gene.

8. A vector containing the nucleic acid construct according to claim 6.

9. A method of preparing a delivery vector for delivery of a CFTR gene to a mammal, which method comprises formulating the nucleic acid construct according to claim 6 into a delivery vector suitable for administration to said mammal.

* * * * *

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
       (A) LENGTH: 21 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO: 1:

AATCCTAACT CTGTCACTTA T                                              21

(2) INFORMATION FOR SEQ ID NO: 2:

(i) SEQUENCE CHARACTERISTICS:
       (A) LENGTH: 28 base pairs

```
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 2:

TAACAATGTG ATCTTAGGCA ATTTACTT                                              28

(2) INFORMATION FOR SEQ ID NO: 3:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

TTAACAATGT GATCT                                                            15

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 4:

CGGGATCCAA GCAAGTACGC ATGATA                                                26

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 5:

CCTTAATTAA GGATCCGAGA ATGTGTGATT TTCTTG                                     36

(2) INFORMATION FOR SEQ ID NO: 6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 6:

TCCCCGCGGA TCCAAGGGAA GATCAGGAAC AAC                                        33

(2) INFORMATION FOR SEQ ID NO: 7:

(i) SEQUENCE CHARACTERISTICS:
        (A) LENGTH: 36 base pairs
        (B) TYPE: nucleic acid
```

```
          (C) STRANDEDNESS: single
          (D) TOPOLOGY: linear (ii) MOLECULE TYPE: other nucleic acid
          (A) DESCRIPTION: /desc = "Synthetic oligonucleotide (xi) SEQUENCE DESCRIPTION: SEQ ID NO: 7:

CCTTAATTAA GGATCCATAG TGTGAAAACC ACTGAC                              36

(2) INFORMATION FOR SEQ ID NO: 8:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide (xi) SEQUENCE DESCRIPTION: SEQ ID NO: 8:

TCCCCGCGGA TCCTCCAAAG TACATGCTTC TTC                                 33

(2) INFORMATION FOR SEQ ID NO: 9:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide (xi) SEQUENCE DESCRIPTION: SEQ ID NO: 9:

CCTTAATTAA GGATCCTCAT CTTTATCTTC ATTGTC                              36

(2) INFORMATION FOR SEQ ID NO: 10:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide (xi) SEQUENCE DESCRIPTION: SEQ ID NO: 10:

TCCCCGCGGA TCCTAACTCA TTGTACTGAC GAG                                 33

(2) INFORMATION FOR SEQ ID NO: 11:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "Synthetic oligonucleotide (xi) SEQUENCE DESCRIPTION: SEQ ID NO: 11:

GTACTTTGGA ATCAG                                                     15

(2) INFORMATION FOR SEQ ID NO: 12:

(i) SEQUENCE CHARACTERISTICS:
          (A) LENGTH: 15 base pairs
```

-continued (B) TYPE: nucleic acid
   (C) STRANDEDNESS: single
   (D) TOPOLOGY: linear (ii) MOLECULE TYPE: other nucleic acid
   (A) DESCRIPTION: /desc = "Synthetic oligonucleotide (xi) SEQUENCE DESCRIPTION: SEQ ID NO: 12:

CTGATTCCAA AGTAC                  15

(2) INFORMATION FOR SEQ ID NO: 13:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: other nucleic acid
   (A) DESCRIPTION: /desc = "Synthetic oligonucleotide (xi) SEQUENCE DESCRIPTION: SEQ ID NO: 13:

GTCACTTATT AACAATGTGA               20

(2) INFORMATION FOR SEQ ID NO: 14:

(i) SEQUENCE CHARACTERISTICS:
   (A) LENGTH: 20 base pairs
   (B) TYPE: nucleic acid
   (C) STRANDEDNESS: single
   (D) TOPOLOGY: linear (ii) MOLECULE TYPE: other nucleic acid
   (A) DESCRIPTION: /desc = "Synthetic oligonucleotide (xi) SEQUENCE DESCRIPTION: SEQ ID NO: 14:

TCACATTGTT AATAAGTGAC               20

(2) INFORMATION FOR SEQ ID NO: 15:

(i) SEQUENCE CHARACTERISTICS:
   (A) LENGTH: 18 base pairs
   (B) TYPE: nucleic acid
   (C) STRANDEDNESS: single
   (D) TOPOLOGY: linear (ii) MOLECULE TYPE: other nucleic acid
   (A) DESCRIPTION: /desc = "Synthetic oligonucleotide (xi) SEQUENCE DESCRIPTION: SEQ ID NO: 15:

TCTTAGGCAA TTTACTTA                18

(2) INFORMATION FOR SEQ ID NO: 16:

(i) SEQUENCE CHARACTERISTICS:
   (A) LENGTH: 18 base pairs
   (B) TYPE: nucleic acid
   (C) STRANDEDNESS: single
   (D) TOPOLOGY: linear (ii) MOLECULE TYPE: other nucleic acid
   (A) DESCRIPTION: /desc = "Synthetic oligonucleotide (xi) SEQUENCE DESCRIPTION: SEQ ID NO: 16:

TAAGTAAATT GCCTAAGA                18

(2) INFORMATION FOR SEQ ID NO: 17:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 17:

ACAATGTGAT CTTAGGCAAT TTACTT                                              26

(2) INFORMATION FOR SEQ ID NO: 18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 18:

AAGTAAATTG CCTAAGATCA CATTGT                                              26

(2) INFORMATION FOR SEQ ID NO: 19:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 19:

AATCCTAACT CTGTCACTTA TTAACAATGT GATC                                     34

(2) INFORMATION FOR SEQ ID NO: 20:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 20:

GATCACATTG TTAATAAGTG ACAGAGTTAG GATT                                     34

(2) INFORMATION FOR SEQ ID NO: 21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 21:

GTACTTTGGA ATCAGACAGA CCTGGCTGG                                           29

(2) INFORMATION FOR SEQ ID NO: 22:

```
    (i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic oligonucleotide (xi) SEQUENCE DESCRIPTION: SEQ ID NO: 22:

CCAGCCAGGT CTGTCTGATT CCAAAGTAC                              29

(2) INFORMATION FOR SEQ ID NO: 23:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 23:

AATCCTAACT CTGTCACTTA TTAACAATGT GATCTTAGGC AATTTACTT        49

(2) INFORMATION FOR SEQ ID NO: 24:

(i) SEQUENCE CHARACTERISTICS:
        (A) LENGTH: 200 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 24:

ATCTCATATT CTACTTCATC TTTATCTTCA TTGTCAACTG TCAGGTAGCA ATATATGATG    60

GAAGAAGCAT GTACTTTGGA ATCAGACAGA CCTGGCTGGA ATCCTAACTC TGTCACTTAT   120

TAACAATGTG ATCTTAGGCA ATTTACTTAA TCTCTCTGAA CCTCAGCTAC TCTCGTCAGT   180

ACAATGAGTT ATCCTTATCT                                              200

(2) INFORMATION FOR SEQ ID NO: 25:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

ACAATGTGAT CTT                                               13

(2) INFORMATION FOR SEQ ID NO: 26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

TGTCACTTAT CTTGC                                             15
```